(12) United States Patent
Zha et al.

(10) Patent No.: US 9,169,294 B2
(45) Date of Patent: *Oct. 27, 2015

(54) ANTI-ANGIOGENIC MOLECULES, NANOSTRUCTURES AND USES THEREOF

(71) Applicant: Northwestern University, Evanston, IL (US)

(72) Inventors: Runye H. Zha, Chicago, IL (US); Ming Zhang, Glencoe, IL (US); Samuel I. Stupp, Chicago, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/202,682

(22) Filed: Mar. 10, 2014

(65) Prior Publication Data

US 2014/0256635 A1 Sep. 11, 2014

Related U.S. Application Data

(60) Provisional application No. 61/776,158, filed on Mar. 11, 2013.

(51) Int. Cl.
| | | |
|---|---|---|
| *A61K 38/00* | (2006.01) |
| *A61P 35/00* | (2006.01) |
| *C07K 14/515* | (2006.01) |
| *C12N 5/00* | (2006.01) |
| *C12N 5/02* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/08* | (2006.01) |

(52) U.S. Cl.
CPC ....................... *C07K 7/08* (2013.01)

(58) Field of Classification Search
CPC ........................................................ C07K 7/08
See application file for complete search history.

(56) References Cited

U.S. PATENT DOCUMENTS

| | | | | |
|---|---|---|---|---|
| 5,905,023 | A * | 5/1999 | Sager et al. ..................... | 435/456 |
| 7,371,719 | B2 * | 5/2008 | Stupp et al. .................. | 424/185.1 |
| 7,390,526 | B2 * | 6/2008 | Stupp et al. ................... | 427/2.27 |
| 7,452,679 | B2 * | 11/2008 | Stupp et al. ..................... | 435/7.1 |
| 7,491,690 | B2 * | 2/2009 | Stupp et al. ..................... | 514/1.1 |
| 7,534,761 | B1 * | 5/2009 | Stupp et al. ..................... | 514/1.1 |
| 7,544,661 | B2 * | 6/2009 | Stupp et al. ..................... | 514/1.1 |
| 7,554,021 | B2 * | 6/2009 | Stupp et al. ..................... | 428/113 |
| 7,851,445 | B2 * | 12/2010 | Stupp et al. .................. | 514/13.3 |
| 8,114,834 | B2 * | 2/2012 | Hsu et al. ........................ | 514/3.2 |
| 8,748,569 | B2 * | 6/2014 | Stupp et al. ................... | 530/300 |
| 2005/0118678 | A1 * | 6/2005 | Mayo ............................ | 435/69.1 |
| 2011/0144022 | A1 | 6/2011 | Brigati et al. | |

OTHER PUBLICATIONS

Arnaoutova and Kleinman, "In vitro angiogenesis: endothelial cell tube formation on gelled basement membrane extract," Nature Protocols, 2010, 5, 628-635.
Bailey et al., "Biological functions of maspin," Journal of Cellular Physiology, 2006, 209, 617-624.
Bass et al., "Binding of extracellular maspin to beta-1 integrins inhibits vascular smooth muscle cell migration," Journal of Biological Chemistry, 2009, 284, 27712-27720.
Binetruy-Tournaire et al., "Identification of a peptide blocking vascular endothelial growth factor (VEGF)—mediated angiogenesis," The EMBO Journal 19, 1525-1533 (2000).
Carmeliet and Jain, "Angiogenesis in cancer and other diseases," Nature, 2000, 407, 249-257.
Cella et al., "Maspin is physically associated with beta-1 integrin regulating cell adhesion in mammary epithelial cells," The FASEB Journal, 2006, 20, 1510-1512.
Cui et al., "Self-assembly of peptide amphiphiles: From molecules to nanostructures to biomaterials," Biopolymers, 2010, 94, 1-18.
Eisenberg et al., "The design, synthesis, and crystallization of an alpha—helical peptide," Proteins: Structure, Function, and Genetics, 1986, 1, 16-22.
Endsley et al., "Maspin, the molecular bridge between the plasminogen activator system and beta1 Integrin that facilitates cell adhesion," Journal of Biological Chemistry, 2011, 286, 24599-24607.
Forns et al., "Induction of protein-like molecular architecture by monoalkyl hydrocarbon chains," Biopolymers, 2000, 54, 531-546.
Fuguet et al., "Critical micelle concentration of surfactants in aqueous buffered and unbuffered systems," Analytica Chimica Acta, 2005, 548, 95-100.
Geng et al., "Shape effects of filaments versus spherical particles in flow and drug delivery," Nature Nanotechnology, 2007, 2, 249-255.
Ghanaati et al., "Dynamic in vivo biocompatibility of angiogenic peptide amphiphile nanofibers," Biomaterials, 2009, 30, 6202-6212.
Hanahan and Weinberg, "The hallmarks of cancer," Cell, 2000, 100, 57-70.
Ho and DeGrado, "Design of a 4-helix bundle protein: Synthesis of peptides which self-associate into a helical protein," Journal of the American Chemical Society, 1987, 109, 6751-6758.
Jiang et al., "The internal structure of self-assembled peptide amphiphiles nanofibers," Soft Matter, 2007, 3, 454-462.
Kerbel and Folkman, "Clinical translation of angiogenesis inhibitors," Nature Reviews Cancer, 2002, 2, 727-739.
Khan et al., "Self-assembling glucagon-like peptide 1-mimetic peptide amphiphiles for enhanced activity and proliferation of insulin-secreting cells," Acta Biomateriali, 2012, 8, 1685-1692.

(Continued)

*Primary Examiner* — Marcela M Cordero Garcia
(74) *Attorney, Agent, or Firm* — Casimir Jones S.C.

(57) ABSTRACT

The disclosure is generally directed toward the design and synthesis of peptide amphiphile (PA) molecules that comprises a peptide configured to inhibit angiogenesis. The peptide amphiphile comprises a hydrophobic tail, peptide sequence capable of beta-sheet formation; and a peptide, wherein the peptide is configured to inhibit angiogenesis. Optionally the PA further comprises a flexible linker between the peptide sequence capable of beta-sheet formation and the peptides. Further this disclosure is directed to nanostructures comprising peptide amphiphiles configured to inhibit angiogenesis.

21 Claims, 13 Drawing Sheets

(56) References Cited

OTHER PUBLICATIONS

Koehl and Levitt, "Structure-based conformational preferences of amino acids," Proceedings of the National Academy of Sciences of the United States of America, 1999, 96, 12524-12529.

Law et al., "The high resolution crystal structure of the human tumor suppressor maspin reveals a novel conformational switch in the g-helix," Journal of Biological Chemistry, 2005, 280, 22356-22364.

MacPHEE and Woolfson, "Engineered and designed peptide-based fibrous biomaterials," Current Opinion in Solid State and Materials Science, 2004, 8, 141-149.

Maione et al., "Inhibition of angiognnesis by recombinant human platelet factor-4 and related peptides," Science, 1990, 247, 77-79.

Matson et al., "Peptide self-assembly for crafting functional biological materials," Current Opinion in Solid State and Materials Science, 2011, 15, 225-235.

Mayo et al., "Designed beta-sheet peptides that inhibit proliferation and induce apoptosis in endothelial cells," Angiogenesis, 2001, 4, 45-51.

Noonan et al., "Angiogenesis and cancer prevention: a vision," Recent Results in Cancer Research, 2007, 174, 219-224.

Paramonov et al., "Self-assembly of peptide-amphiphile nanofibers: The roles of hydrogen bonding and amphiphilic packing," Journal of the American Chemical Society 128, 7291-7298 (2006).

Qin and Zhang, "Maspin regulates endothelial cell Adhesion and migration through an integrin signaling pathway," Journal of Biological Chemistry, 2010, 285, 32360-32369.

Ravenhill et al., "G-helix of maspin mediates effects on cell migration and adhesion," Journal of Biological Chemistry, 2010, 285, 36285-36292.

Sakamoto et al., "Inhibition of angiogenesis and tumor growth by a synthetic laminin peptide, CDPGYIGSR-NH2," Cancer Research 51, 1991, 903-906.

Shi et al., "Blocking tumor growth, invasion, and metastasis by maspin in a syngeneic breast cancer model," Cancer Research, 2001, 61, 6945-6951.

Storrie et al., "Supramolecular crafting of cell adhesion," Biomaterials, 2007, 28, 4608-4618.

Tolsma et al., "Peptides derived from two separate domains of the matrix protein thrombospondin-1 have anti-angiogenic activity," Journal of Cell Biology, 1993, 122, 497-511.

Velichko et al., "Molecular simulation study of peptide amphiphile self-assembly," The Journal of Physical Chemistry B, 2008, 112, 2326-2334.

Webber et al., "Emerging peptide nanomedicine to regenerate tissues and organs," Journal of Internal Medicine, 2010, 267, 71-88.

Webber et al., "Supramolecular nanostructures that mimic VEGF as a strategy for ischemic tissue repair," Proceedings of the National Academy of Sciences of the United States of America, 2011, 108, 13438-13443.

West et al., "Angiogenesis assays using chick chorioallantoic membrane," Methods in Molecular Medicine 46, 107-129 (2001).

Whitmore et al., "Protein secondary structure analyses from circular dichroism spectroscopy: Methods and reference databases," Biopolymers, 2008, 89, 392-400.

Woltering et al., "Somatostain analogues inhibit angiogenesis in the chick chorioallantoic membrane," Journal of Surgical Research, 1991, 50, 245-251.

Zhang et al., "Maspin is an angiogenesis inhibitor," Nature Medicine, 2000, 6, 196-199.

Zou et al., "Maspin, a serpin with tumor-suppressing activity in human mammary epithelial cells," Science, 1994, 263, 526.

\* cited by examiner

FIG. 6A

|  | Alpha Helix | Beta Sheet | Beta Turn | Random Coil |
|---|---|---|---|---|
| MMPA | 23.7% | 25.7% | 12.8% | 37.8% |
| MMPep | 9.1% | 30.6% | 15.3% | 44.9% |
| Scrambled | 19.9% | 31.6% | 11.1% | 37.4% |

FIG. 6
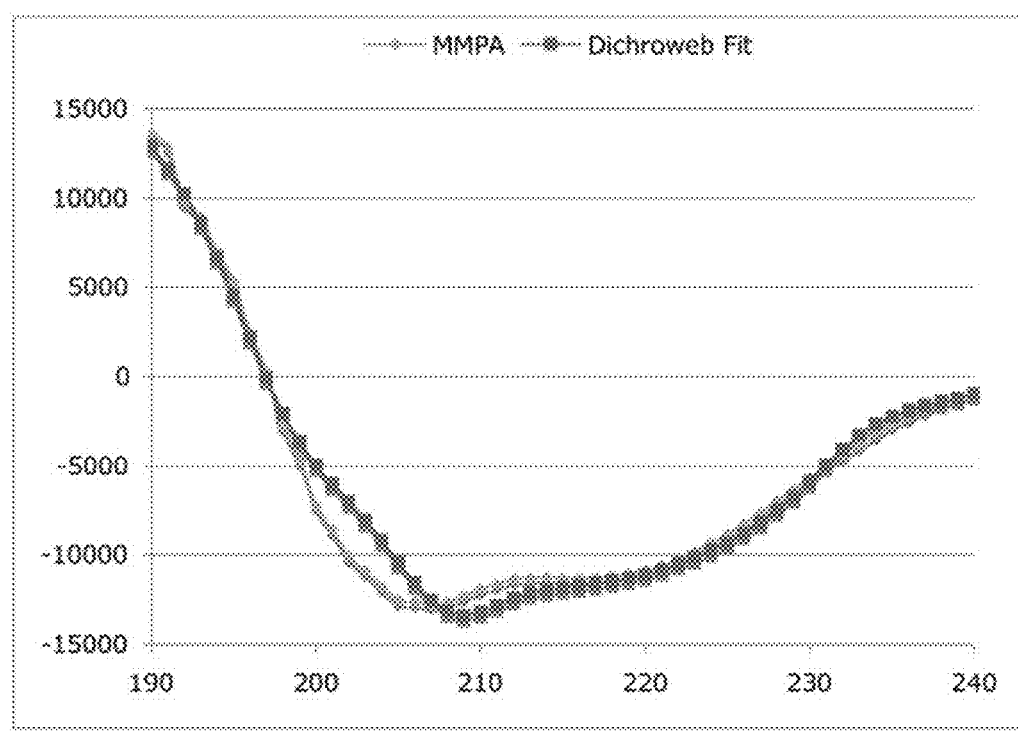
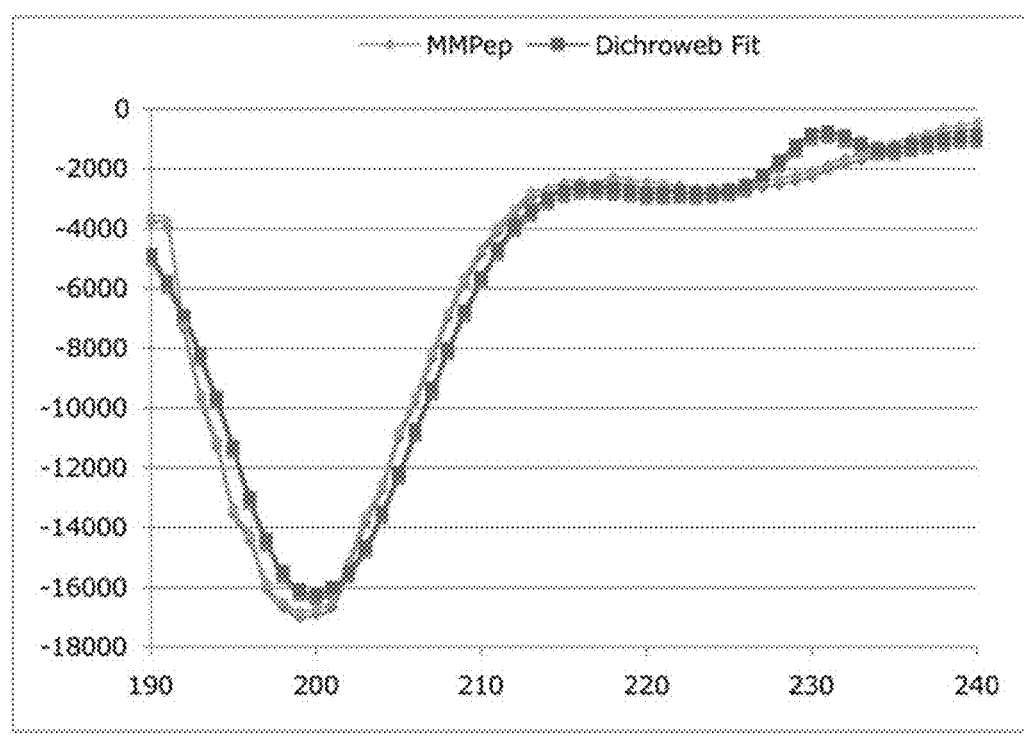

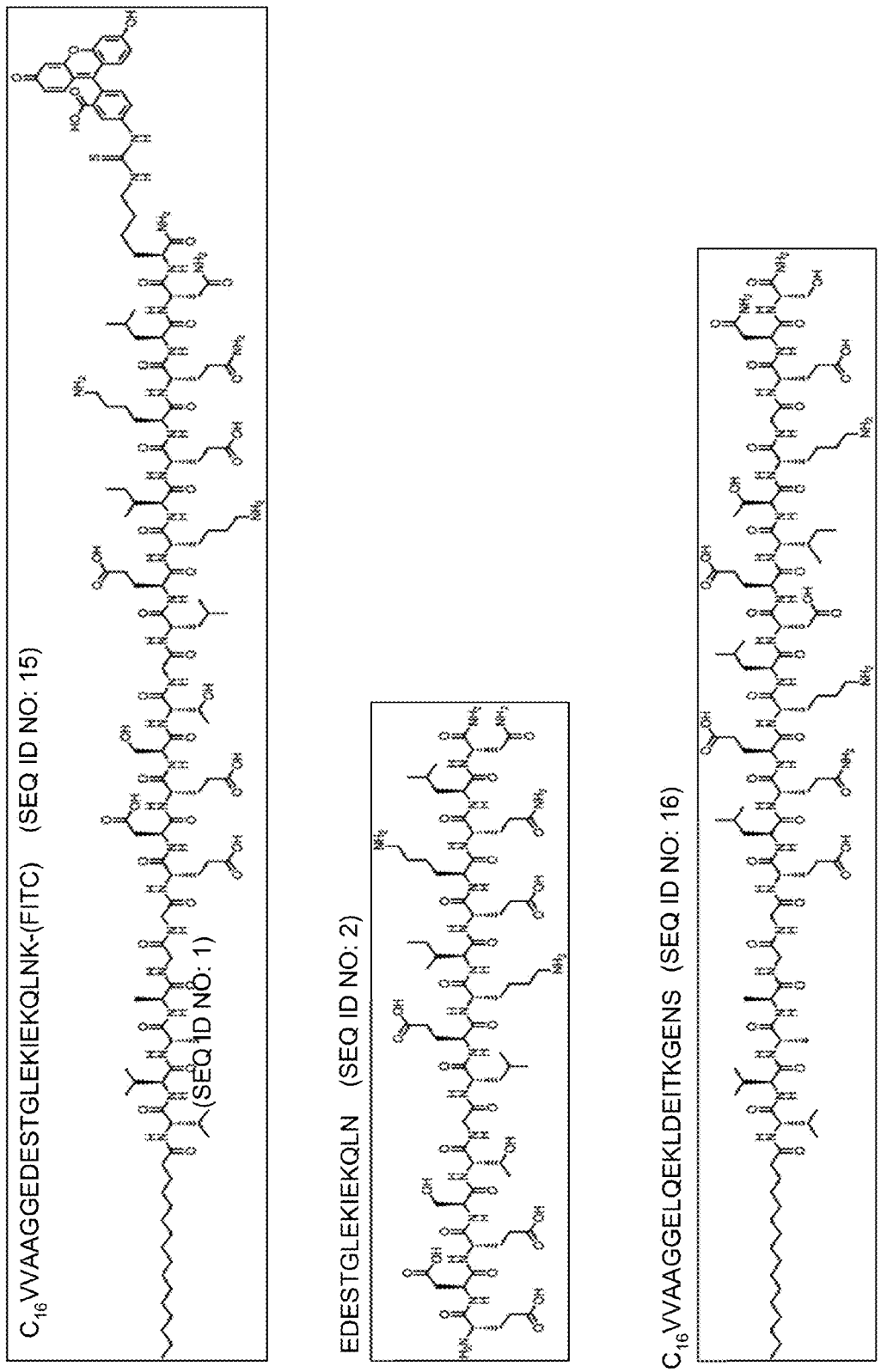

SEQUENCE LISTING

```
<160> NUMBER OF SEQ ID NOS: 20

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1
```

```
Glu Ser Thr Gly Leu Glu Lys Ile Glu Lys Gln
1               5                   10
```

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

```
Glu Asp Glu Ser Thr Gly Leu Glu Lys Ile Glu Lys Gln Leu Asn
1               5                   10                  15
```

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

```
Cys Asp Pro Gly Tyr Ile Gly Ser Arg
1               5
```

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

```
Leu Tyr Lys Lys Ile Ile Lys Lys Leu Leu Glu Ser
1               5                   10
```

<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: Xaa indicates cysteine residues that may be
      replaced by alanine for ease of synthesis

<400> SEQUENCE: 5

```
Asn Ile Pro Pro Ile Thr Xaa Val Gln Asn Gly Leu Arg Tyr
1               5                   10
```

<210> SEQ ID NO 6
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa indicates cysteine residues that may be
      replaced by alanine for ease of synthesis
<220> FEATURE:
<221> NAME/KEY: MISC_FEATURE
<222> LOCATION: (10)..(10)
<223> OTHER INFORMATION: Xaa indicates cysteine residues that may be
      replaced by alanine for ease of synthesis

<400> SEQUENCE: 6

```
Ser Pro Trp Ser Ser Xaa Ser Val Thr Xaa Gly Asp Gly Val Ile Thr
1               5                   10                  15

Arg Ile Arg

<210> SEQ ID NO 7
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa indicates cysteine residues that may be
      replaced by alanine for ease of synthesis
<220> FEATURE:
<221> NAME/KEY: MISC_FEATURE
<222> LOCATION: (10)..(10)
<223> OTHER INFORMATION: Xaa indicates cysteine residues that may be
      replaced by alanine for ease of synthesis

<400> SEQUENCE: 7

Ser Pro Trp Asp Ile Xaa Ser Val Thr Xaa Gly Gly Gly Val Gln Lys
1               5                   10                  15

Arg Ser Lys

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Asn Gly Val Gln Tyr Arg Asn
1               5

<210> SEQ ID NO 9
<211> LENGTH: 13
<212> TYPE: PRT
<213> ORGANISM: Artificial Sequence
<220> FEATURE:
<223> OTHER INFORMATION: Synthetic

<400> SEQUENCE: 9

His Asn Arg Thr Pro Glu Asn Phe Pro Cys Lys Asn Leu
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Phe Cys Tyr Trp Lys Val Cys Trp
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11
```

Phe Cys Phe Trp Lys Thr Cys Thr
1               5

<210> SEQ ID NO 12
<211> LENGTH: 33
<212> TYPE: PRT
<213> ORGANISM: Artificial Sequence
<220> FEATURE:
<223> OTHER INFORMATION: Synthetic

<400> SEQUENCE: 12

Ala Asn Ile Lys Leu Ser Val Gln Met Lys Leu Phe Lys Arg His Leu
1               5                   10                  15

Lys Trp Lys Ile Ile Val Lys Leu Asn Asp Gly Arg Glu Leu Ser Leu
            20                  25                  30

Asp

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Ala Thr Trp Leu Pro Pro Arg
1               5

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Glu Leu Gln Glu Lys Leu Asp Glu Ile Thr Lys Gly Glu Asn Ser
1               5                   10                  15

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

Val Val Ala Ala Gly Gly Glu Asp Glu Ser Thr Gly Leu Glu Lys Ile
1               5                   10                  15

Glu Lys Gln Leu Asn Lys
            20

<210> SEQ ID NO 16
<211> LENGTH: 21
<212> TYPE: PRT
<213> ORGANISM: Artificial Sequence
<220> FEATURE:
<223> OTHER INFORMATION: Synthetic

<400> SEQUENCE: 16

Val Val Ala Ala Gly Gly Glu Leu Gln Glu Lys Leu Asp Glu Ile Thr
1               5                   10                  15

Lys Gly Glu Asn Ser
            20

```
<210> SEQ ID NO 17
<211> LENGTH: 21
<212> TYPE: PRT
<213> ORGANISM: Artificial Sequence
<220> FEATURE:
<223> OTHER INFORMATION: Synthetic

<400> SEQUENCE: 17

Val Val Ala Ala Gly Gly Glu Asp Glu Ser Thr Gly Leu Glu Lys Ile
1               5                   10                  15

Glu Lys Gln Leu Asn
            20

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Val Val Ala Ala
1

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Val Val Ala Ala Gly Gly
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(3)
<223> OTHER INFORMATION: Polar
<220> FEATURE:
<221> NAME/KEY: MISC_FEATURE
<222> LOCATION: (5)..(5)
<223> OTHER INFORMATION: Apolar
<220> FEATURE:
<221> NAME/KEY: MISC_FEATURE
<222> LOCATION: (6)..(7)
<223> OTHER INFORMATION: Polar
<220> FEATURE:
<221> NAME/KEY: MISC_FEATURE
<222> LOCATION: (8)..(8)
<223> OTHER INFORMATION: Apolar
<220> FEATURE:
<221> NAME/KEY: MISC_FEATURE
<222> LOCATION: (9)..(11)
<223> OTHER INFORMATION: Polar

<400> SEQUENCE: 20

Xaa Xaa Xaa Gly Xaa Xaa Xaa Xaa Xaa Xaa Xaa
1               5                   10
```

ANTI-ANGIOGENIC MOLECULES, NANOSTRUCTURES AND USES THEREOF

CROSS REFERENCE TO RELATED APPLICATIONS

The present invention claims the priority to U.S. Provisional Patent Application No. 61/776,158, filed Mar. 11, 2013, which is incorporated by reference in its entirety.

STATEMENT OF GOVERNMENT INTEREST

The invention was made with government support under grant numbers CA079736 and U54 CA151880 awarded by the National Institutes of Health. The government has certain rights in the invention.

FIELD OF THE DISCLOSURE

The disclosure is generally directed toward the design, synthesis and use of peptide amphiphile (PA) molecules that comprises a peptide configured to inhibit angiogenesis.

BACKGROUND

The growth of a tumor to clinically malignant dimensions requires angiogenesis, the sprouting of new blood vessels from pre-existing vasculature.[1-3] Not only is angiogenesis crucial for tumor growth due to oxygen and nutrient demands, it is also essential for the progression of tumor malignancy. Angiogenesis inhibitors, used either in conjunction with or in place of traditional cytotoxic chemotherapies, have shown promise in restricting tumor growth and have thus become a topic of much research. [4]

Due to the prohibitive cost of synthesizing and purifying protein therapeutics, peptides can potentially be clinical game-changers, especially if their activity and potency match that of whole protein. Rationally designed molecules that conjugate a bioactive peptide to a self-assembly region have shown much promise in mimicking the bioactivity of proteins. These molecules, known as peptide amphiphiles (PAs), typically consist of a hydrophobic alkyl tail, a peptide sequence capable of β-sheet formation, and the peptide.[13-15] Optionally there may be a flexible peptide sequence as linker between the peptide sequence capable of beta-sheet formation, and the peptide. PAs have been shown to self-assemble in aqueous solution into nanostructures, including high aspect-ratio nanofibers comprised of a hydrophobic core and stabilized by beta-sheet formation down the long axis. [16,17] These nanofibers can display a high surface density of peptides,[18] stabilize peptide secondary structure,[19] and improve therapeutic retention in tissue.[20,21] Thus, such PAs can be functionally protein-mimetic with regards to activity and potency. For example, protein-mimetic PAs bearing peptides derived from vascular endothelial growth factor and glucagon-like peptide 1 have shown remarkable bioactivity in stimulating angiogenesis and promoting insulin release, respectively.[19,22]

SUMMARY OF THE INVENTION

The present invention discloses compositions comprising (a) a hydrophobic tail; (b) a peptide sequence capable of beta-sheet formation; and (c) a peptide, wherein the peptide is configured to inhibit angiogenesis.

In certain embodiments the compositions may optionally comprise a flexible linker between the peptide sequence capable of beta-sheet formation and the peptide. The flexible linker may be a peptide. In certain embodiments the flexible linker is the peptide GG In certain embodiments the hydrophobic tail is a C6-C22 alkyl group. In certain examples the hydrophobic tail is linear.

In certain embodiments the peptide sequence capable of beta-sheet formation comprises VVAA (SEQ ID NO: 18).

In certain embodiments the peptide is a protein-derived peptide, a cytokine analogue peptide, a hormone analogue peptide, an engineered peptide, or a combinatorial peptide. The peptide may comprise a PPPXHPPHPPP (SEQ ID NO: 20) sequence of amino acids, wherein P is a polar amino acid, H is an apolar amino acid and X is a glycine. Additionally the peptide may comprise a mapsin g-helix. The peptide may also comprise ESTGLEKIEKQ (SEQ ID NO: 1) or EDESTGLEKIEKQLN (SEQ ID NO: 2).

The present disclosure also discloses nanostructures compositions comprising (a) a hydrophobic tail; (b) a peptide sequence capable of beta-sheet formation; and (c) a peptide, wherein the peptide is configured to inhibit angiogenesis. Optionally the nanostructures may comprise a second peptide amphiphile. The nanostructures may form a nanofiber having a high aspect-ratio. Further the nanostructures may have a hydrophobic core. The nanostructures may also be stabilized by beta-sheet formation. The nanostructures may also have a high surface density of peptides. Further the nanostructures may stabilize the peptide secondary structure.

The present disclosure also discloses methods of inhibiting angiogenesis by contacting endothelial cells with the compositions or nanostructures disclosed herein in an amount effective to inhibit angiogenesis. Further angiogenesis may be inhibited by at least 5%, at least 10%, at least 15%, at least 20%, at least 25%, at least 35%, at least 40%, at least 45%, at least 50%, at least 55%, at least 60%, at least 65%, at least 70%, at least 75%, at least 80%, at least 85%, at least 90%, or at least 95%.

BRIEF DESCRIPTION OF THE DRAWINGS

FIGS. 6A-D. Summary of circular dichroism fits obtained for PAs and peptide using DichroWeb online analysis tool FIG. 7. Chemical structure of FITC-labeled MMPA, as well as MMPep and ScramPA without FITC.

DETAILED DESCRIPTION

Figure 1:
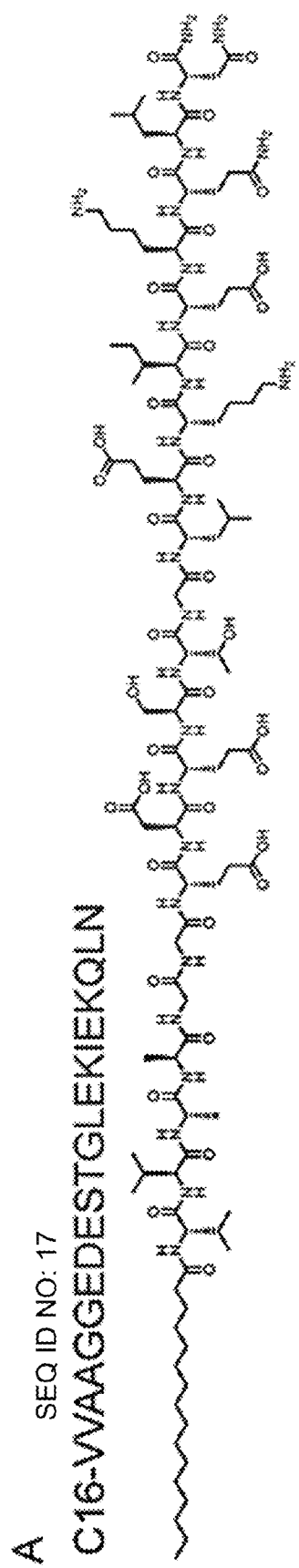
FIGS. 1A-F. (A) Structure of MMPA, with the bioactive sequence shown in red, the beta-sheet and flexible linker sequence shown in blue, and the hydrophobic alkyl tail shown in black. (B) Shift in peak nile red emission as a function of concentration, indicating a CAC between 1-2.5 µM for MMPA and 0.5-2.5 µM for ScramPA in PBS. (C) Circular dichroism of PAs and peptide in 0.1×PBS, showing that MMPep exhibits primarily random coil conformation while MMPA and ScramPA have increased alpha-helix signature. ScramPA exhibits primarily beta-sheet conformation. (D) Conventional TEM of MMPA and (E) ScramPA in PBS at 1 mM, showing the existence of high aspect ratio nanostructures. (F) SAXS of PAs and peptides in PBS at 1 mM, indicating that MMPA and ScramPA assemble into a mixture of cylindrical and flat nanofibers while MMPep does not assemble appreciably in solution.
Figure 1:
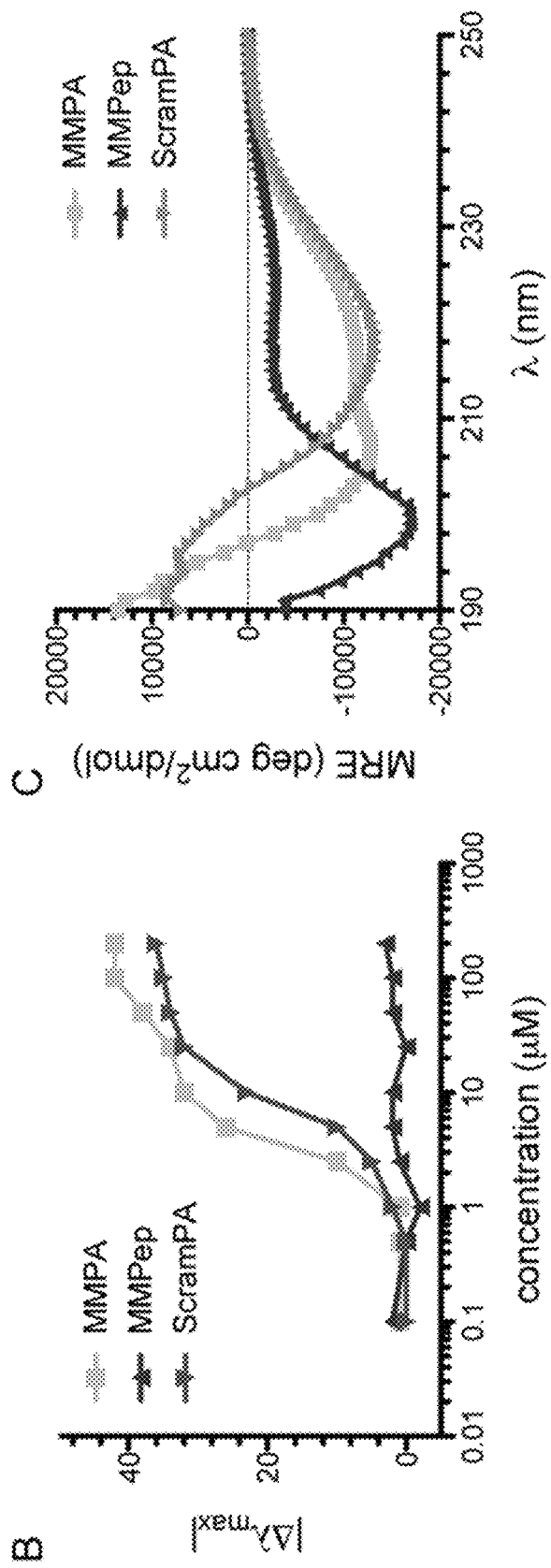
Figure 1:
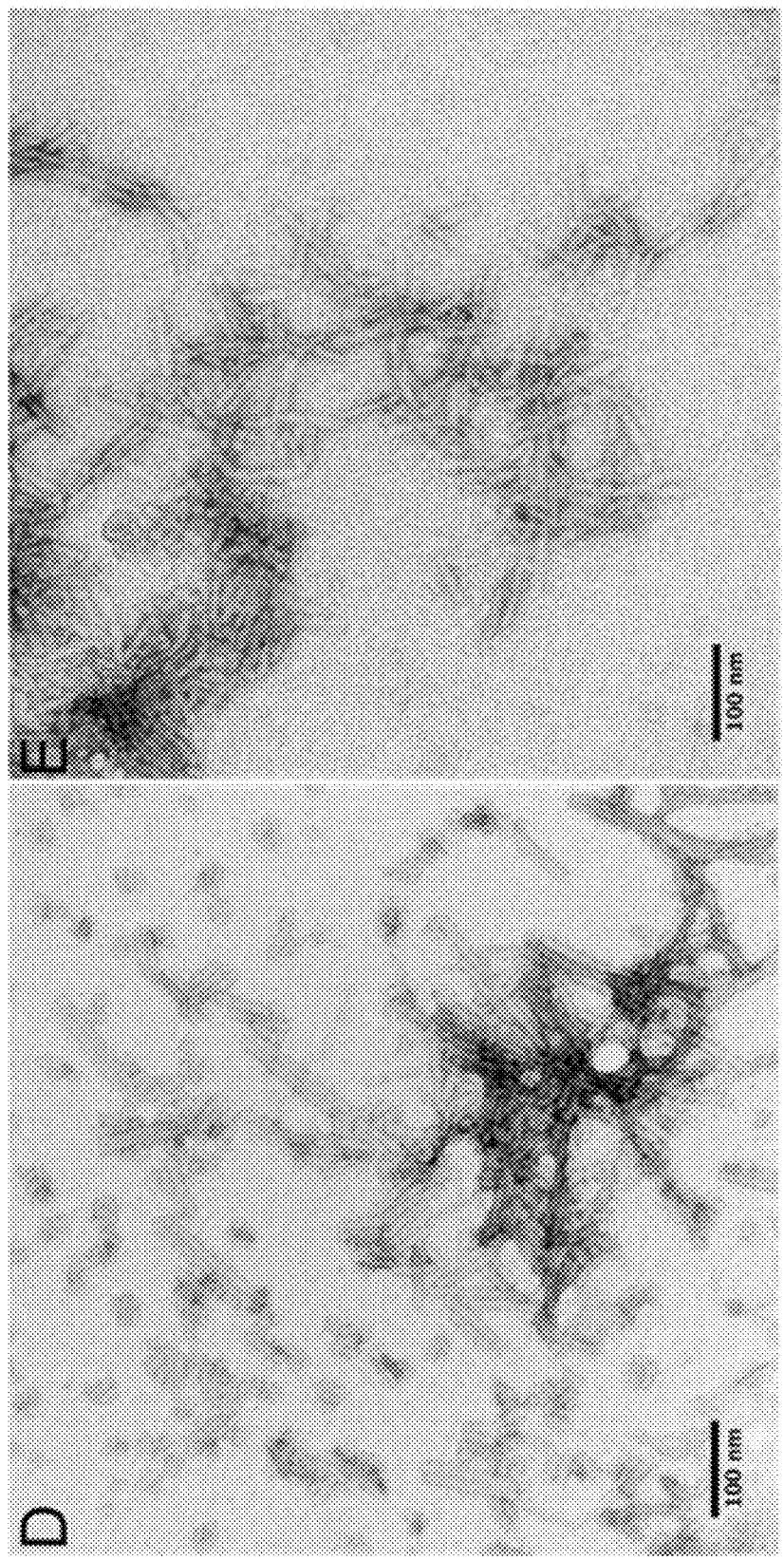
Figure 1:
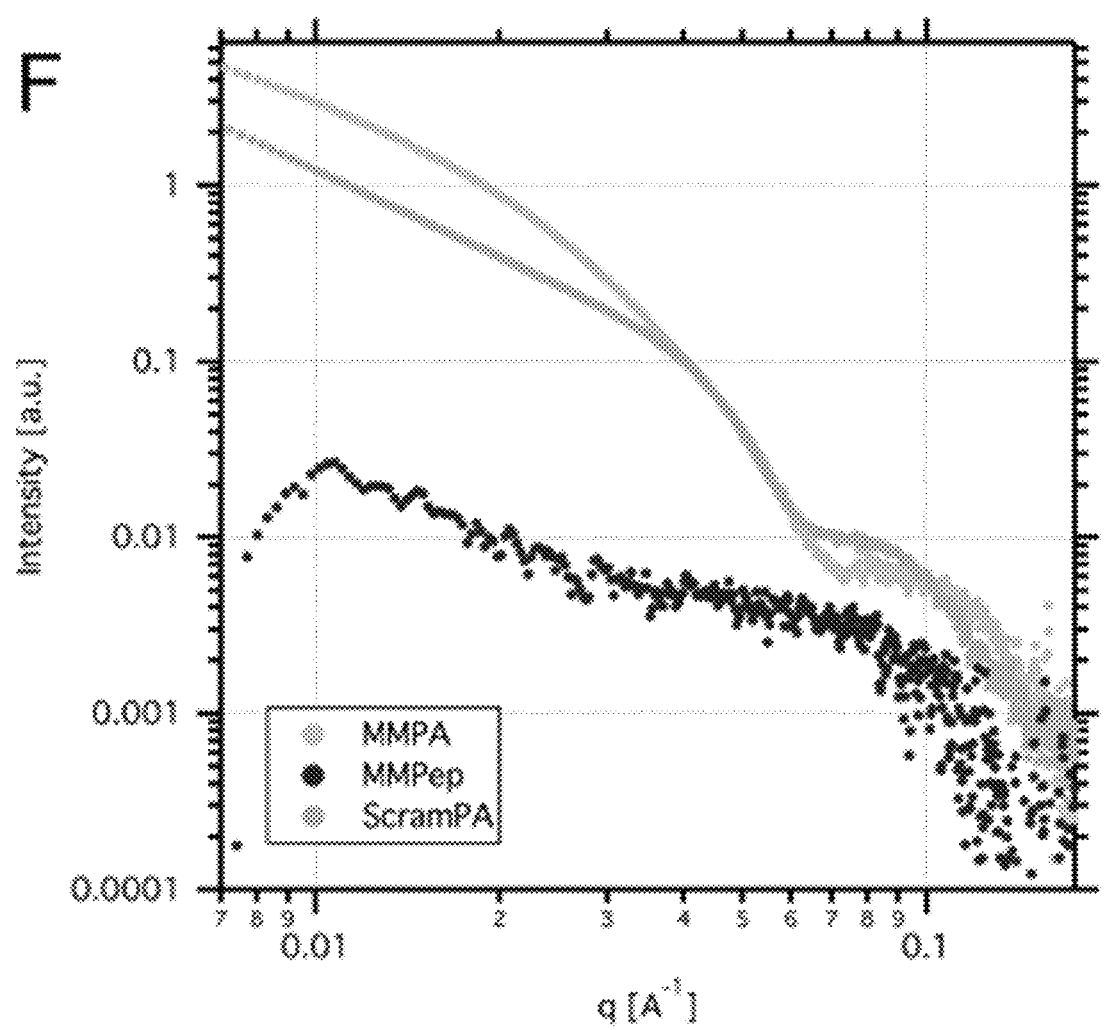

The disclosure is generally directed toward the design, synthesis and use of peptide amphiphile (PA) molecules that comprises a peptide configured to inhibit angiogenesis. In vitro and in vivo assays confirm that PAs bearing peptides configured to inhibit angiogenesis exhibit potent anti-angiogenic capabilities.

Peptides Configured to Inhibit Angiogenesis

There are a number of different classes and specific examples of peptides configured to inhibit angiogenesis. The following are examples and not intended to be limiting.

Protein-Derived Peptides consist of amino acid sequences taken directly from proteins that show anti-angiogenic activity and are minimally modified (e.g. for ease of synthesis). Such sequences may be discovered by methods including but not limited to identification of unique motifs from protein crystal structure and investigation of strategically altered proteins. Examples of protein-derived anti-angiogenic peptides include:

| Peptide | Protein Origin | Reference | SEQ ID NO: |
|---|---|---|---|
| CDPGYIGSR-NH2 | laminin | Sakamoto, 1991 | 3 |
| LYKKIIKKLLES | platelet factor-4 | Malone, 1990 | 4 |
| NIPPITC*VQNGLRY | collagen-I | Tolsma, 1993 | 5 |
| SPWSSC*SVTC*GDGVITRIR | thrombospondin-1 | Tolsma, 1993 | 6 |
| SPWDIC*SVTC*GGGVQKRSK | thrombospondin-1 | Tolsma, 1993 | 7 |
| NGVQYRN | thrombospondin-1 | Tolsma, 1993 | 8 |
| HNRTPENFPCKNL | angiostatin | Brigati, 2011 | 9 |
| ESTGLEKIEKQ | maspin | Refs. 5-12 | 1 |

*indicates cysteine residues that may be replaced by alanine for ease of synthesis Maspin, a 42 kDa secreted serine protease inhibitor protein, has come under particular scrutiny due to its potency in limiting tumor growth and metastasis. [5-7] As a class II tumor suppressor protein, maspin expression is significantly down-regulated during the malignant progression of breast and prostate cancers. While the anti-cancer activity of maspin is multifunctional, its role as a potent angiogenesis inhibitor is mediated through interaction with β1 integrin receptor and the urokinase-type plasminogen activator (uPA)/uPA receptor (uPAR) complex, which results in increased adhesion and decreased migration of endothelial cells. [8-10] Recent research has shown that these functions of maspin require its "g-helix" motif.[11] This g-helix, originally identified by the protein crystal structure, is structurally distinct from the reactive serpin loop (RSL) of maspin.[12] However, a 15-mer peptide encompassing the g-helix sequence and two residues on either side (residues 236-250) was able to inhibit migration of multiple cell lines in a β1 integrin-dependent manner similar to full-length maspin, albeit at much higher concentrations. [8,11]

Cytokine and Hormone Analogue Peptides mimic the sequence, function, and/or structure of small cell-signaling proteins, peptides, and glycoproteins that show anti-angiogenic activity. Such analogue peptides may contain amino acid sequences directly taken from cytokines and hormones with no modification or with rational substitutions/additions. Examples of cytokine and hormone analogue peptides include:

| Peptide | Protein Origin | Reference | SEQ ID NO: |
|---|---|---|---|
| FCYWKVCW | somatostatin | Woltering, 1991 | 10 |
| FCFWKTCT | somatostatin | Woltering, 1991 | 11 |

Engineered Peptides are amino acid sequences that are not directly derived from naturally occurring proteins, peptides, or glycoproteins but may contain functional elements from such molecules that mediate anti-angiogenic activity. Such functional elements may include but are not limited to general secondary structure, patterns of charge/hydrophobicity/hydrophilicity, presence of specific amino acids in key locations, and particular arrangement of components so as to have maximum efficacy in inhibiting angiogenesis. Engineered peptides may include non-natural modifications where appropriate so as to enhance function and efficacy. Examples of engineered peptides include:

| Peptide | Reference | SEQ ID NO: |
|---|---|---|
| ANIKLSVQMKLFKRHLKWKIIVKL NDGRELSLD | Mayo, 2001 | 12 |

Combinatorial Peptides are amino acid sequences discovered by methods that utilize peptide libraries and repeated applications of defined screening techniques/criteria (e.g. phage display) in order to identify peptides with anti-angiogenic activity. Such peptides may or may not have homology to naturally occurring angiogenesis inhibitors. Examples of combinatorial peptides include:

| Peptide | Reference | SEQ ID NO: |
|---|---|---|
| ATWLPPR | Binetruy-Tournaire, 2000 | 13 |

PAs Self-assemble at μM Concentrations

The g-helix of maspin is an 11-residue motif presented on the protein periphery and has been shown to be crucial for decreasing motility and increasing adhesion, two functions which act together on endothelial cells to inhibit angiogenesis.[11,12] The 15-residue peptide encompassing the g-helix plus two additional residues on either side (MMPep) was synthesized as previously reported.[11] Mapsin-mimetic peptide amphiphile (MMPA) was rationally designed by conjugating MMPep to a C16VVAA self-assembly region via flexible glycine linker (FIG. 1A). ScramPA consists of the same self-assembly region and flexible linker but a randomly scrambled version of the MMPep sequence. The critical aggregation assembly concentration (CAC) of MMPA, MMPep, and ScramPA in PBS was determined by observing solvatochromic nile red incorporation into hydrophobic domains, which manifests as a blueshift in peak emission. Results indicate that MMPA is capable of forming hydrophobic domains encapsulating nile red at concentrations between 1 μM-2.5 μM, while ScramPA may begin to encapsulate nile red at concentrations as low as 500 nM (FIG. 1B). Like many surfactants, PA self-assembly is driven by hydrophobic collapse of alkyl tails. However, the inclusion of a VVAA (SEQ ID NO: 18) peptide segment increases the hydrophobic portion of the molecule and also adds a degree of intermolecular interaction, as valine residues have high propensity for beta-sheet formation. [24] Furthermore, the presence of valine residues immediately adjacent to the hydrophobic tail promotes formation of high aspect ratio nanofibers stabilized by beta-sheets parallel to the long axis.[25] As a result, these the CAC values of PAs measured here are orders of magnitude lower than those of surfactants such as hexadecyltrimethylammonium bromide[26] and may be even lower in the presence of serum proteins, which could act as nucleation points for aggregation. Accordingly, MMPep does not show any appreciable aggregation at concentrations investigated (up to 200 μM). Circular dichroism (CD) further suggests PA self-assembly in the presence of ions, as both MMPA and ScramPA exhibit significantly less random coil signature than MMPep (FIG. 1C).

Conventional TEM was performed to investigate the morphology of self-assembled nanostructures in solution. Results show that MMPA and ScramPA form short nanofibers at 1 mM in PBS (FIGS. 1D and 1E) but do not show any nanostructure formation for MMPep. SAXS at 1 mM displays relatively low scattering signal for MMPep, which is in accordance with lack of self-assembly and nanostructure formation. SAXS further indicates that the MMPA and ScramPA nanofibers are a mixture of cylindrical and ribbon-like shapes based on a slope of approximately −1.75 in the Guinier region at low q values (FIG. 1F). The flatter shape of the Guinier region seen for ScramPA may be due to nanostructure aggregation resulting from aggressive PA self-assembly. However, it should be emphasized that detailed characterization of PA nanostructure morphology at low concentrations (<100 μM) remains an unfortunately difficult challenge and that such nanostructures are likely to vary from those seen at higher concentrations by SAXS and TEM.

MMPA Self-assembly Stabilizes g-Helix Secondary Structure

Figure 6D:
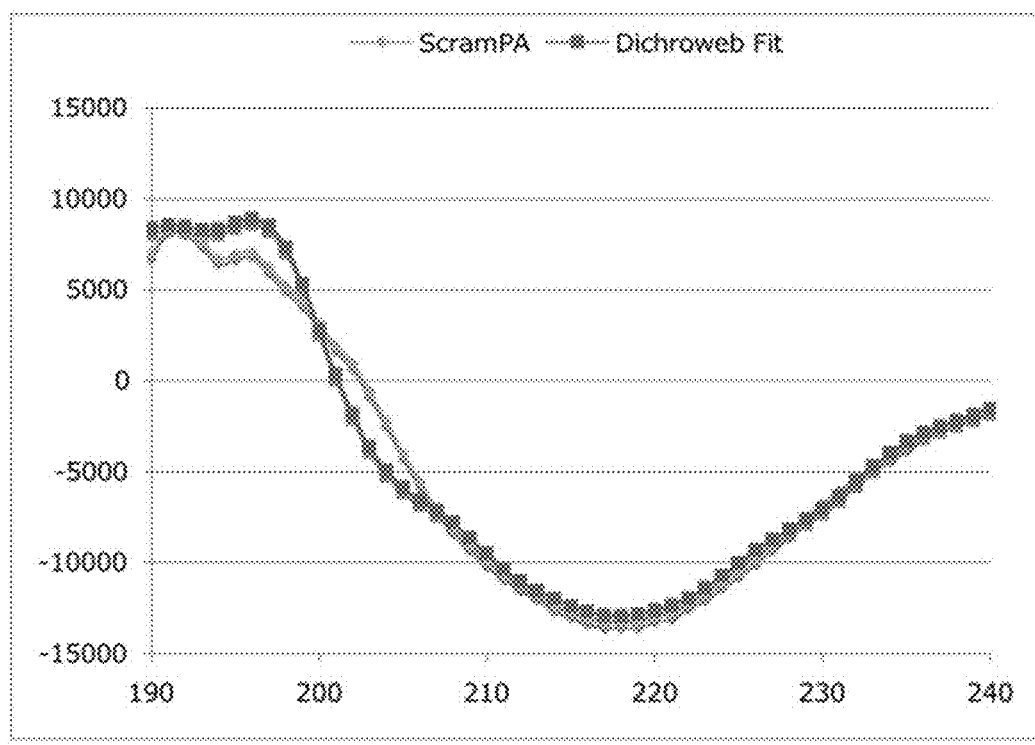

The arrangement of polar (P) and apolar (H) residues in the maspin g-helix can be depicted as PPPXHPPHPPP (SEQ ID NO: 20), where X represents glycine. This periodically hydrophobic sequence is characteristic of amphipathic alpha-helices and despite the helix-breaking tendency of glycine residues,[27] structural data from crystalized maspin confirms that the g-helix exhibits alpha-helical secondary structure.[12] Thus, CD was further used to examine the secondary structure formation of MMPep, MMPA, and ScramPA (FIG. 1C). PAs and peptide concentrations were examined at 100 μM in 0.1X PBS. Fitting results obtained with the DichroWeb algorithm (FIG. 6) show that MMPep displays primarily random coil conformation with very little alpha-helical character, while MMPA exhibits significantly enhanced α-helix signature. In comparison, ScramPA also shows increased alpha-helical character over MMPep but additionally displays higher beta-sheet signature. These results suggest that the g-helix sequence alone does not take on the native helical structure found in maspin protein but that PA self-assembly stabilizes and promotes alpha-helix conformation. Similar stabilization of helical structure has been previously observed in PA systems[19,22,28] and likely results from clustering of helices facilitated by molecular self-assembly. Because amphipathic helices such as the g-helix exhibit a hydrophobic face and a polar face, secondary structure stability is greatly improved by coil-coil interactions. Studies showing increased helicity with increasing peptide concentration confirm this hypothesis and further implicate the role of nanostructure self-assembly in stabilizing the native g-helix conformation.[29,30]

MMPA Nanostructures Bind to Cells and Recapitulate Multiple Functions of Maspin

Figure 2:
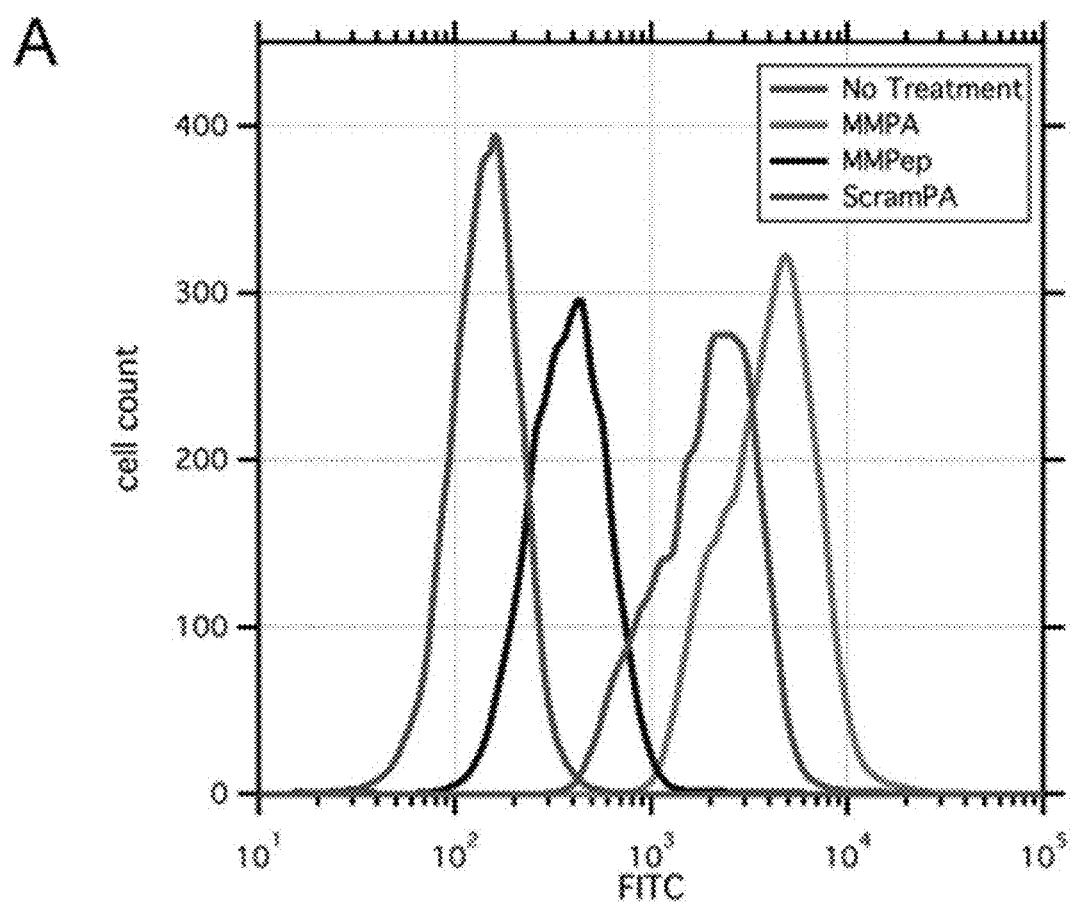
FIGS. 2A-E. (A) FACS analysis of HUVEC fluorescence after treatment with FITC-labeled PAs and peptide. Results show that cell binding is most effective for MMPA but also occurs non-specifically with ScramPA while MMPep binds to cells significantly less effectively than PA nanostructures. Differences in the level of cell binding is also shown in confocal microscopy images of cells treated with (B) PBS control, (C) FITC-labeled MMPep, (D) FITC-labeled MMPA, and (E) FITC-labeled ScramPA.
Figure 2:
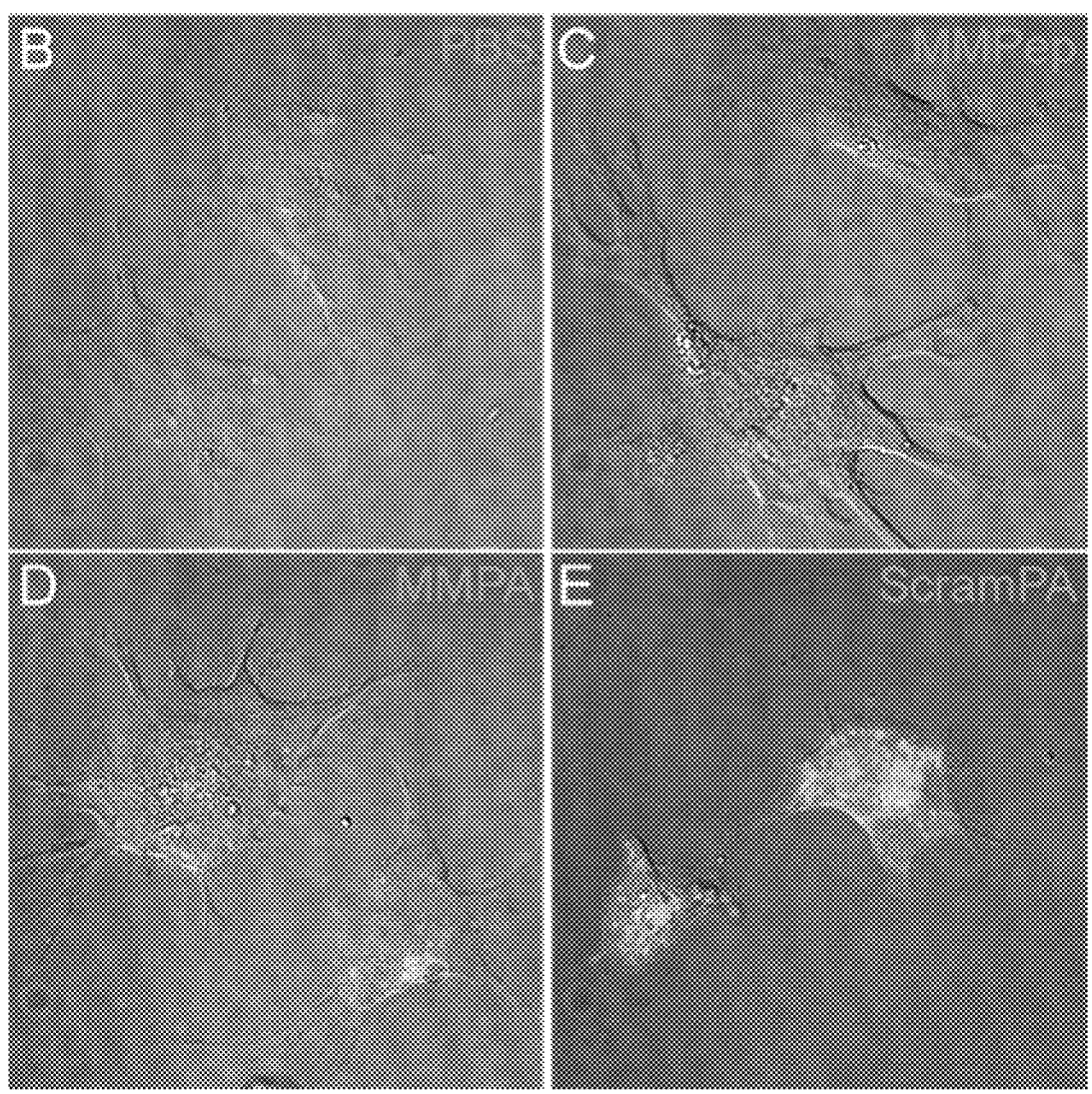

Previous studies have shown that maspin interacts with 131 integrin receptors, thereby triggering pathways that inhibit cell migration.[9,31,32] Specifically, the migration inhibiting activity of the g-helix peptide alone has been shown to depend on 131 integrin interaction.[11] Therefore, we investigated the ability of PAs and peptide to bind to HUVECs in culture. Fluorescent analogues of MMPA, MMPep, and ScramPA molecules were synthesized by coupling FITC to an additional lysine residue on the C-terminus (FIG. 7) and were mixed as a small fraction to the corresponding non-fluorescent molecule for visualization. FACS shows cells treated with MMPA and ScramPA to be significantly more fluorescent than untreated control or those treated with MMPep (FIG. 2A). The median FITC intensity per cell for MMPA, ScramPA, and MMPep was 28.7, 14.1, and 2.6 times that of untreated control, respectively. Confocal microscopy confirms that both MMPA and ScramPA bind to HUVEC membranes and are additionally present in the interior of the cells (FIGS. 2B-2E). This result suggests that nanostructure self-assembly facilitates cell binding, possibly by stabilizing the native g-helix conformation or by displaying locally high signal density on nanostructure surfaces. However, binding of PAs to cells is, in part, non-specific and may simply be a result of ionic interaction between cell surfaces and nanostructures with high surface charge density.

Figure 3:
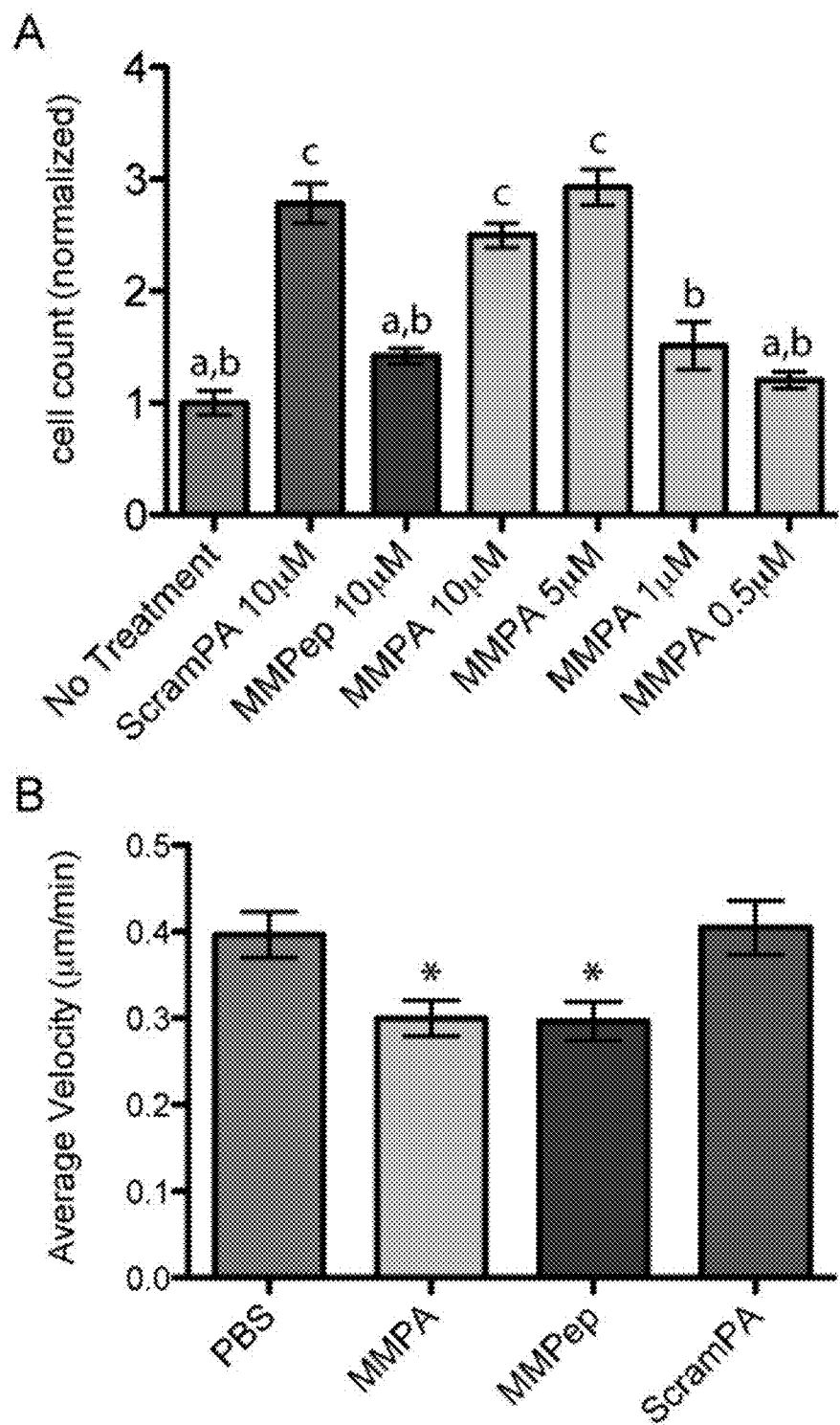
FIGS. 3A-B. (A) Number of HUVECs, as obtained by PicoGreen assay, that remain adhered to FN-coated tissue culture plastic after treatment with PAs or peptide and repeated washing steps. Results are normalized to the mean of the control group and show that MMPA and ScramPA treatments above their CAC non-specifically increase cell adhesion to FN, while MMPep and unassembled PA do not show this effect. Statistical analysis shows that groups a and b are statistically insignificant, groups a and c are statistically significant (P<0.001), and groups b and c are statistically significant (P<0.01). (B) Average velocity of HUVECs on FN-coated glass as measured by time-lapse imaging and manual tracking, showing cells treated with MMPA and MMPep to be statistically less migratory (P<0.05) as compared to PBS control.

To investigate whether PA binding to HUVECs is capable of increasing cell adhesion to extracellular matrix (ECM) in vitro, HUVEC adhesion was characterized by allowing PA or peptide-treated cells to adhere to a FN-coated surface and then quantifying the number of cells that remained attached to the surface after washing. Cells treated with MMPA showed statistically significant increase in adhesion to the FN surface over untreated controls at 5 μM or 10 μM PA concentrations (FIG. 3A). The difference between these two higher concentrations was insignificant. However, treatment concentrations that are below the measured CAC of MMPA (i.e. ≤1 μM) were not effective at increasing adhesion. Moreover, increased cell adhesion is non-specific, as cells treated with ScramPA showed similar behavior at 10 μM. Because the concentration of PA in solution was extremely low, increased adhesion is not likely to be caused by significant coverage of the FN surface by PAs but is more likely due to the strong non-specific binding of PA to the cell surface. This phenomenon covers the cell with attachment points, as PA nanostructures can likely adhere via charge interaction and mechanical nanofiber entanglement to ECM components as well. Thus, PA nanostructures effectively mimic certain focal adhesion functions.

It is worthwhile to note that MMPep, which does not self-assemble or bind strongly to cells, was unable to improve cell adhesion over untreated controls.[11] Similar results were obtained previously by Ravenhill and coworkers, suggesting that though the ability of maspin to increase cell adhesion and decrease cell motility relies on having an intact g-helix, only the latter activity is directly mediated by activation of β1 integrin by the g-helix. Endsley and coworkers showed that the ability of maspin to increase cell adhesion requires formation of a supercomplex between maspin and its β1 integrin receptor with urokinase-type plasminogen activator (uPA) and its cell surface receptor (uPAR).[10] As the g-helix motif is not functionally involved in bridging maspin and uPA/uPAR, it is unsurprising that MMPep cannot recapitulate this maspin functionality. Thus, while cell migration and cell adhesion are frequently seen as intimately related activities, both should be recognized as distinctly different phenomena with potentially separate triggers that work in concert to affect overall cell behavior. Live-cell imaging to observe HUVEC migration in response to bFGF stimulus and PA or peptide treatment did indeed confirm the ability of both MMPep and MMPA to significantly decrease cell motility over untreated controls (FIG. 3B). The average cell migration speed (measured over at least 2 hrs and up to 8 hrs) was 0.30 μm/min for both MMPA and MMPep treatment conditions compared with 0.40 μm/min for PBS control. Interestingly, the speed of cell migration with ScramPA treatment was not significantly different from control despite stronger cell attachment show by in vitro adhesion assay. Since previous studies have shown that the g-helix sequence alone is sufficient and necessary to inhibit cell migration in vitro via β1-dependent mechanisms, it is unsurprising that both MMPep and MMPA were able to affect cell motility while ScramPA could not.

MMPA Inhibits Tube Formation in vitro and Blocks Angiogenesis in vivo

Figure 4:
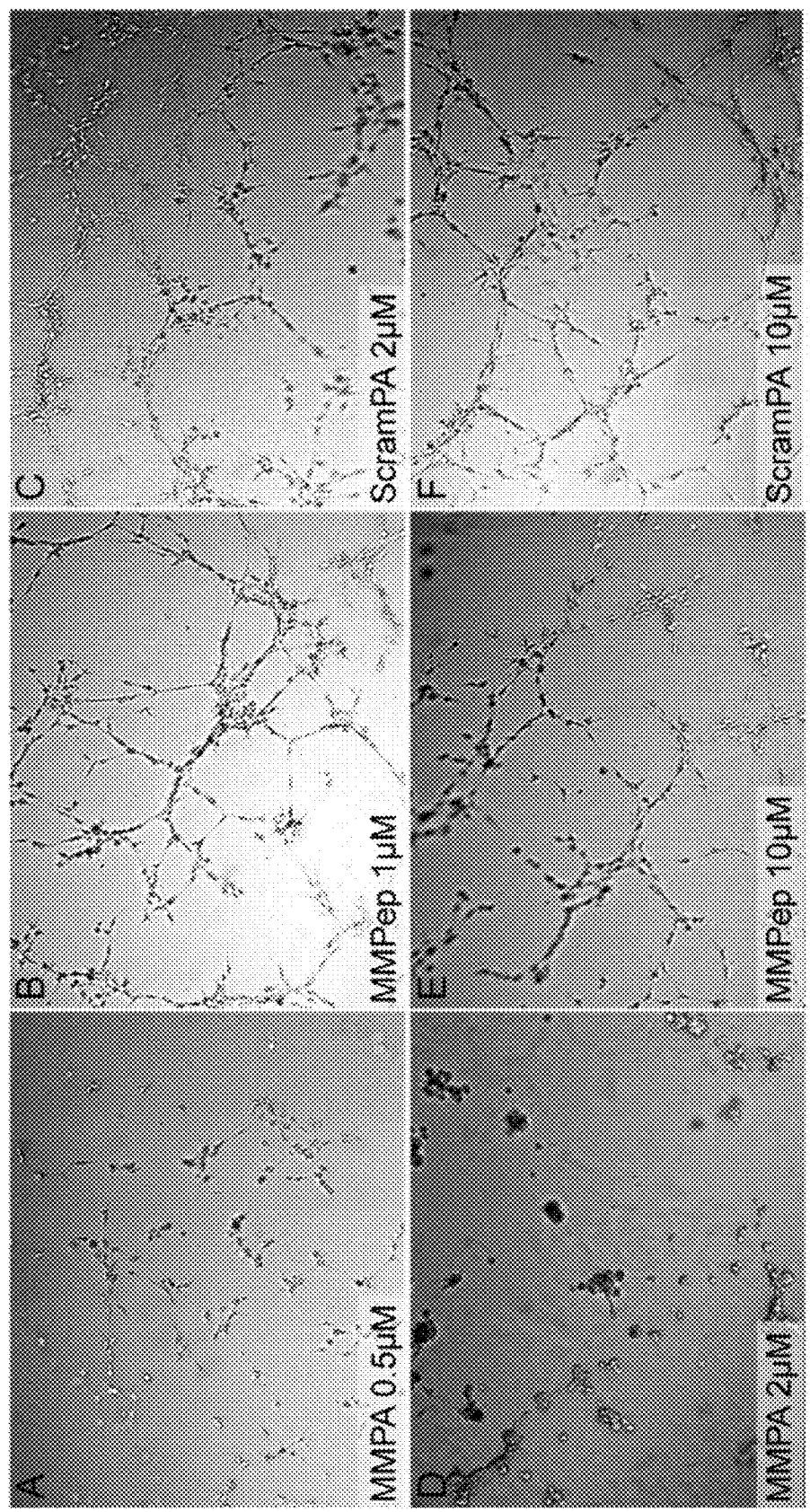
FIGS. 4A-F. Tube formation of HUVECs on matrigel as imaged 5 hrs after addition of MMPA (A, D), MMPep (B, E), and ScramPA (C, F). Results show that MMPA is capable of inhibiting tube formation at sub-micromolar concentrations while MMPep is slightly effective at greater than 10 µM. ScramPA does not show any efficacy in blocking tube formation at any concentrations investigated.

Well-established models exist for assessing angiogenesis in vitro and in vivo. [33,34] Tubulogenesis, the formation of tube-like structures by HUVECs on matrigel, was used to observe the anti-angiogenic potency of PAs and peptide in a quasi-3D system. Based on images obtained 5 hrs after addition of treatments (FIG. 4), MMPA was found to be effective in inhibiting tube formation at even sub-micromolar concentrations, which is on par with the bioactivity of native full-length maspin in literature. [8] MMPep partially inhibited tube formation at higher concentrations (10 μM), while SCRAM PA did not inhibit tube formation even at high concentrations despite non-specific binding to cells. This effect suggests that g-helix sequence is required for anti-angiogenic activity in vitro. Moreover, PA nanostructures displaying the g-helix show drastically improved efficacy over the g-helix peptide alone.

Figure 5:
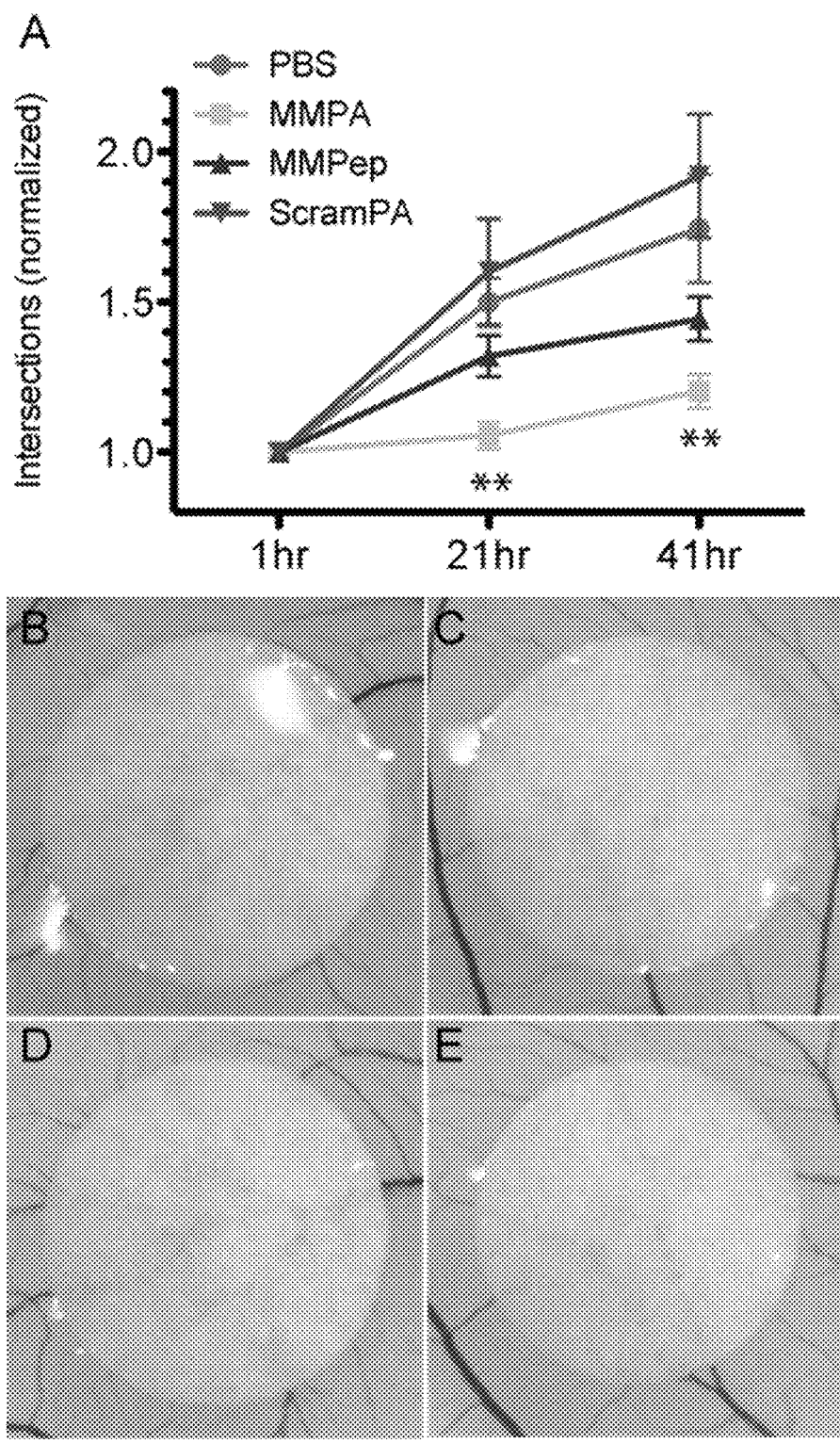
FIGS. 5A-E. (A) Angiogenesis in chick embryo CAM as quantified by counting the number of vessels intersecting the circumference of filter paper circles at 1, 21, and 41 hr after application of treatment. For each sample, counts at later time points are normalized to initial time point (t=1 hr). Statistical analysis indicates that MMPA significantly decreases angiogenesis at both 21 hr and 41 hr time points (P<0.01). Sample images of PBS treatment at (B) 1 hr and (D) 21 hr as compared to PA treatment at (C) 1 hr and (E) 21 hr.

The efficacy of PAs or peptide in blocking angiogenesis in vivo was investigated using a chick embryo chorioallantoic membrane (CAM) assay. Because the CAM is highly angiogenic, especially in stages of early development, concentrated PA or peptide treatment (1 mM in PBS) was delivered from filter paper circles placed onto the shell-less embryo CAM on embryonic day 5. The number of blood vessels intersecting each filter paper perimeter was then counted at 21 hrs and 42 hrs. FIG. 5A shows the increase in intersections, normalized to the initial count, for each treatment condition. Only MMPA was found to significantly reduce angiogenesis over PBS controls at both time points, while the anti-angiogenic activity of MMPep was present but is statistically insignificant. Interestingly, ScramPA-treated samples showed a trend towards increased angiogenesis over PBS control. This trend is not statistically significant due to large sample variation but can potentially correlate with increased endothelial cell adhesion in vitro caused by ScramPA.

The potency of MMPA in blocking angiogenesis both in vitro and in vivo indicates that incorporation of the g-helix motif into self-assembled nanostructures drastically improves its maspin-mimetic function. Like the g-helix peptide alone, MMPA nanostructures decrease cell motility on FN. However, MMPA nanostructures not only stabilize the native g-helix secondary structure by effectively concentrating g-helix moieties at nanostructure surfaces, such nanostructures also bind aggressively to endothelial cell surfaces and significantly improve adhesion. While PAs bearing a scrambled g-helix sequence also exhibit these latter effects, the combination of specific g-helix-mediated inhibition of cell migration with non-specific increase of cell adhesion allows MMPA to mimic multiple functions of full-length maspin and block angiogenesis with high potency.

We have developed a PA that incorporates the maspin g-helix functional motif and shows potent anti-angiogenic bioactivity in vitro and in vivo. This maspin-mimetic PA self-assembles in aqueous environments to form nanostructures that display concentrated signaling density and stabilize the native g-helix conformation. In vitro cell assays show that maspin-mimetic PA nanostructures exhibit the g-helix mediated migration inhibition bioactivity of full-length maspin. Furthermore, maspin-mimetic PA nanostructures recapitulate the ability of full-length maspin to increase cell adhesion, a function not mediated through the g-helix, via non-specific interactions with cells and extracellular matrix. As maspin-mimetic PA captures multiple functions of the full length protein, it was effective in blocking tubulogenesis in vitro at concentrations comparable to that of native maspin and was also effective at inhibiting angiogenesis in vivo in the chicken embryo chorioallantois.

EXAMPLES

PA Synthesis and Purification

Peptide and PAs were synthesized using standard fluoren-9-ylmethoxycarbonyl (Fmoc) solid-phase peptide synthesis. The maspin-mimetic peptide (MMPep) consists of the maspin g-helix sequence plus two residues on either end (EDESTGLEKIEKQLN (SEQ ID NO: 1)) while the maspin-mimetic PA (MMPA) includes an additional C16VVAAGG (SEQ ID NO: 19) on the N-terminus. PA with the same C16VVAAGG (SEQ ID NO: 19) region but a scrambled g-helix sequence (ScramPA) of ELQEKLDEITKGENS (SEQ ID NO: 14) was additionally synthesized. All molecules were synthesized on rink amide resin and thus display an amide on the C-terminus. Fluorescent versions of the peptide and PAs were synthesized by incorporating a C-terminus lysine with N-methyltrityl side group protection, orthogonally deprotecting the side group, and reacting with fluorescein isothiocyanate (FITC) while on resin. PAs and peptide were dissolved with 20% hexafluoro-2-propanol in acidic 18.2 MOhm pure (MilliQ) water and were purified using reversed-phase high-performance liquid chromatography in an acidic methanol/water gradient containing 0.1% trifluoroacetic acid at a starting condition of 20% methanol. Purified PAs and peptide were lyophilized and stored at −20° C. until use.

Peptide content for non-fluorescent peptide and PAs was analyzed (AIBioTech) in order to establish an accurate conversion between mass concentration and molarity. Stock solutions of peptide and PAs were prepared by dissolving molecules in phosphate buffered saline (PBS) at 1 mM for at least overnight at room temperature prior to use.

Critical Assembly Concentration Determination by Nile Red Incorporation.

The self-assembly of peptide and PAs was assessed by incorporation of hydrophobic solvatochromic nile red (NR) fluorophore, which exhibits an emission blueshift in hydrophobic environments. MMPA, MMPep, or ScramPA solutions ranging from 100 nM to 200 µM concentration in PBS were made from stock solutions and NR dissolved in ethanol was diluted 200-fold into solutions to a final concentration of 500 nM. Using a NanoLogHJ spectrofluorometer, samples were excited at 550 nm and spectra were obtained between from 580 nm-750 nm. Blueshift was plotted against concentration to determine the critical assembly concentration.

Secondary Structure Characterization by Circular Dichroism.

The secondary structure of peptide and PAs was probed using circular dichroism (CD) at 22° C. Peptide and PAs were diluted to 100 µM in 0.1×PBS from stock solution immediately prior to measurement with a JASCO J-715 CD spectrophotometer in a 1 mm pathlength quartz cuvette. From the mean residue ellipticity data, α-helix and β strand content was estimated using the DichroWeb online analysis algorithm.[23]

Nanostructure Imaging by Electron Microscopy.

Samples for transmission electron microscopy (TEM) were prepared from 1 mM PA or peptide stock solution by placing 5 µL solution onto a 300 mesh copper grid with an amorphous carbon support film (Electron Microscopy Sciences). The solution was wicked after 2 min, washed twice with MilliQ water, and allowed to dry for 10 min before staining with 2% uranyl acetate. Imaging was performed on a JEOL 1230 TEM with a Hamamatsu ORCA camera at an accelerating voltage of 100 kV.

Nanostructure Determination by Small Angle X-ray Scattering.

Small angle x-ray scattering (SAXS) was used to probe the nanostructure morphology of peptide and PAs at 1 mM concentration in PBS. SAXS measurements were performed using beam line 5ID-D in the DuPont-Northwestern-Dow Collaborative Access Team (DND-CAT) Synchrotron Research Center at the Advanced Photon Source of Argonne National Laboratory. Using a double-crystal monochromator to select an energy of 15 keV, scattering data was collected using a CCD detector (MAR) positioned 245 cm behind the sample. Scattering intensity was recorded in the interval $0.008<q<0.25 \text{ A}^{-1}$ and the wave vector was defined as $q=(4\pi/\lambda)\sin(\theta/2)$, where θ is the scattering angle. Solution samples were loaded in 1.5 mm diameter quartz capillaries with exposure times between 2 and 8 s. The 2D SAXS images collected were azimuthally averaged to produce 1D profiles of intensity using the data reduction program Fit2D. Background scattering of the capillary with only PBS was also collected and was subtracted from sample data prior to data analysis.

Flow Cytometry and Confocal Microscopy to Assess PA Binding.

Stock fluorescent PA and peptide solutions were made by dissolving FITC-labeled molecules in PBS at a concentration of 200 µM (assuming peptide content of 90%). Stock fluorescent solutions were then mixed in equal volumes with 1 mM stock solutions of non-fluorescent PA or peptide solution and allowed to sit overnight at room temperature to make working solutions. Subconfluent human umbilical vein endothelial cells (HUVECs) were incubated for 2 hr in starvation media before detaching with 0.05% trypsin/EDTA. Cells were then spun down to remove trypsin/EDTA and were re-suspended in starvation media at 250,000/mL. Working peptide and PA solutions then added to cell suspensions such that the final concentration corresponded to 10 µM non-fluorescent molecule. After incubating at 37° C. for 30 mins, cells were spun down and resuspended in Hank's balanced salt solution (HBSS) twice. Fluorescence signal of each cell was quantified using a LSRFortessa cell analyzer (BD Biosciences). Cells were also plated on poly-d-lysine coated glass coverslips, fixed with 4% paraformaldehyde, and embedded in mounting media for imaging using an AIR laser scanning confocal microscope (Nikon). Machine parameters were kept constant for all samples in both confocal microscopy and flow cytometry experiments.

Assessment of Cell Adhesion on Fibronectin.

The effect of peptide and PAs on HUVEC adhesion was assessed. Fibronectin from human plasma (Sigma) was dissolved in sterile MilliQ water and was added to tissue culture-treated 96 well plates at 5 µg/cm2, which were then left to dry overnight at room temperature in a sterile laminar flow hood. Coated plates were stored at 4° C. and warmed to 37° C. prior to use. Subconfluent HUVECs were incubated for 2 hr in starvation media (EndoGRO basal media from Millipore supplemented with 0.5% fetal bovine serum and 1× penicillin-streptomycin from Gibco) before detaching with 0.05% trypsin/EDTA. Cells were then spun down to remove trypsin/EDTA and were re-suspended in PBS containing peptide or PA molecules. Cells were incubated in treatment for 30 min at 37° C. and then plated at 15,000 cells/well. After 45 mins, wells were washed once with PBS to detach loosely adhered cells. A PicoGreen assay (Invitrogen) was used to quantify number of cells in each well. Cell counts were normalized to that obtained in wells with no treatment. Statistical analysis was performed in GraphPad Prism software using one-way analysis of variance (ANOVA) with a Bonferroni's Multiple Comparisons post-test comparing all pairs of columns. For all treatment groups, n=4.

Assessment of Cell Migration on Fibronectin.

Fibronectin from human plasma was coated onto tissue culture-treated 4-chamber glass-bottom petri dishes (In Vitro Scientific) at 7 μg/cm2 as previously described. Subconfluent HUVECs were incubated for 2 hr in starvation media before detaching with 0.05% trypsin/EDTA. Cells were then spun down to remove trypsin/EDTA, re-suspended in starvation media, and plated onto glass-bottom petri dishes at a concentration of 4000 cells per chamber. After cells attached (approximately 1 hr at 37° C.), the media was aspirated and replaced with starvation media containing 80 μg/mL basic fibroblast growth factor (bFGF) and 10 μM MMPA, MMPep, or Scram PA. Live-cell imaging was performed on a Nikon BioStation IM at 37° C., and cell migration was quantified manually using a plugin to track the location of the cell nucleus every 30 mins in ImageJ software. ANOVA with a Dunnett's Multiple Comparisons post-test of each treatment condition against control was performed using GraphPad Prism software. For control, MMPA, MMPep, and ScramPA, n=56, 54, 31, and 42 respectively.

Assay of Angiogenesis in vitro by Tube Formation.

Wells of a 96-well plate were coated with ECMatrix solution, and $5 \times 10^3$ HUVECs were plated in triplicate wells in a volume of 50 μL of endothelial growth medium (EGM) containing 0.5% FBS with 50 ng/mL bFGF for 2 hours. MMPA, MMPep, ScramPA treatments at respective dosages were added to the wells for 5 hours. Tube formation was evaluated by phase-contrast microscopy using an Olympus IX-70 microscope (100× magnification) connected to a Diagnostic Instruments Spot RT Camera. Experiments were repeated independently three times.

Characterization of Angiogenesis in vivo by CAM Assay.

In vivo assessment of the anti-angiogenic potential of PAs and peptide was performed using the chicken chorioallantoic membrane (CAM). In this well-established CAM assay, angiogenesis of the extraembryonic allantois was measured at several time points after treatment with PAs or peptide. Fertilized chicken eggs (Sunnyside Hatchery) were received and cultured in a temperature controlled, humidified egg incubator. On embryonic day 3, eggs were cracked into 100 mm sterile petri dishes without breaking the yolk sac and were transferred to a water-jacketed humidified $CO_2$ incubator set to 37° C. On embryonic day 5, 5 μL of treatment (PA, peptide, or scrambled PA dissolved in PBS at 1 mM) or control (PBS) solutions were deposited onto autoclaved filter paper circles ¼" in diameter. Solution-soaked filter paper circles were placed on top of the CAM and digital images were captured using a Nikon stereomicroscope. Vessel density was quantified by counting the number of vessels intersecting the circumference of filter paper circles and is expressed relative to the initial time point. ANOVA with a Dunnett's Multiple Comparisons post-test of each treatment condition against control was performed using GraphPad Prism software. A minimum of n=5 samples was analyzed for each treatment condition at each time point.

The foregoing describes and exemplifies aspects of the invention but is not intended to limit the invention defined by the claims which follow. All of the methods disclosed and claimed herein can be made and executed without undue experimentation in light of the present disclosure. While the materials and methods of this invention have been described in terms of specific embodiments, it will be apparent to those of skill in the art that variations may be applied to the materials and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved.

All patents, publications and references cited herein are hereby fully incorporated by reference. In case of conflict between the present disclosure and incorporated patents, publications and references, the present disclosure should control.

1. Hanahan, D. & Weinberg, R. A. The hallmarks of cancer. *Cell* 100, 57-70 (2000).
2. Carmeliet, P. & Jain, R. K. Angiogenesis in cancer and other diseases. *Nature* 407, 249-257 (2000).
3. Noonan, D. M., Benelli, R. & Albini, A. Angiogenesis and cancer prevention: a vision. *Recent Results in Cancer Research* 174, 219-224 (2007).
4. Kerbel, R. & Folkman, J. Clinical translation of angiogenesis inhibitors. *Nature Reviews Cancer* 2, 727-739 (2002).
5. Zou, Z., Anisowicz, A., Hendrix, M. J. C., Thor, A., Neveu, M., Sheng, S., Rafidi, K., Seftor, E. & Sager, R. Maspin, a serpin with tumor-suppressing activity in human mammary epithelial cells. *Science* 263, 526 (1994).
6. Shi, H. Y., Zhang, W., Liang, R., Abraham, S., Kittrell, F. S., Medina, D., & Zhang, M. Blocking tumor growth, invasion, and metastasis by maspin in a syngeneic breast cancer model. Cancer Research 61, 6945-6951 (2001).
7. Bailey, C. M., Khalkhali-Ellis, Z., Seftor, E. A. & Hendrix, M. J. C. Biological functions of maspin. *Journal of Cellular Physiology* 209, 617-624 (2006).
8. Zhang, M., Volpert, O., Shi, Y. H. & Bouck, N. Maspin is an angiogenesis inhibitor. *Nature Medicine* 6, 196-199 (2000).
9. Qin, L. & Zhang, M. Maspin regulates endothelial cell Adhesion and migration through an integrin signaling pathway. *Journal of Biological Chemistry* 285, 32360-32369 (2010).
10. Endsley, M. P., Hu, Y., Deng, Y., He, X., Warejcka, D. J., Twining, S. S., Gonias, S. L. & Zhang, M. Maspin, the molecular bridge between the plasminogen activator system and beta1 Integrin that facilitates cell adhesion. *Journal of Biological Chemistry* 286, 24599-24607 (2011).
11. Ravenhill, L., Wagstaff, L., Edwards, D. R., Ellis, V. & Bass, R. G-helix of maspin mediates effects on cell migration and adhesion. *Journal of Biological Chemistry* 285, 36285-36292 (2010).
12. Law, R. H. P. Irving, J. A., Buckle, A. M., Ruzyla, K., Buzza, M., Bashtannyk-Puhalovich, T. A., Beddoe, T. C., Nguyen, K., Worrall, D. M., Bottomley, S. P., Bird, P. I., Rossjohn, J. & Whissock, J. C. The high resolution crystal structure of the human tumor suppressor maspin reveals a novel conformational switch in the g-helix. *Journal of Biological Chemistry* 280, 22356-22364 (2005).
13. Cui, H., Webber, M. J. & Stupp, S. I. Self-assembly of peptide amphiphiles: From molecules to nanostructures to biomaterials. *Biopolymers* 94, 1-18 (2010).
14. Webber, M. J., Kessler, J. A. & Stupp, S. I. Emerging peptide nanomedicine to regenerate tissues and organs. *Journal of Internal Medicine* 267, 71-88 (2010).
15. Matson, J. B., Zha, R. H. & Stupp, S. I. Peptide self-assembly for crafting functional biological materials. *Current Opinion in Solid State and Materials Science* 15, 225-235 (2011).
16. Jiang, H., Guler, M. O. & Stupp, S. I. The internal structure of self-assembled peptide amphiphiles nanofibers. *Soft Matter* 3, 454-462 (2007).

17. Velichko, Y. S., Stupp, S. I. & Olvera de la Cruz, M. Molecular simulation study of peptide amphiphile self-assembly. *The Journal of Physical Chemistry B* 112, 2326-2334 (2008).
18. Storrie, H., Guler, M. O., Abu-Amara, S, N., Volberg, T., Rao, M., Geiger, B. & Stupp, S. I. Supramolecular crafting of cell adhesion. *Biomaterials* 28, 4608-4618 (2007).
19. Webber, M. J., Tongers, J., Newcomb, C. J., Marquardt, K. T., Bauersachs, J., Losordo, D. W. & Stupp, S. I. Supramolecular nanostructures that mimic VEGF as a strategy for ischemic tissue repair. *Proceedings of the National Academy of Sciences of the United States of America* 108, 13438-13443 (2011).
20. Ghanaati, S., Webber, M. J., Unger, R. E., Orth, C., Hulvat, J. F., Kiehna, S. E., Barbeck, M., Rasic, A., Stupp, S. I. & Kirkpatrick, C. J. Dynamic in vivo biocompatibility of angiogenic peptide amphiphile nanofibers. *Biomaterials* 30, 6202-6212 (2009).
21. Geng, Y., Dalhaimer, P., Cai, S., Tsai, R., Tewari, M., Minko, T. & Discher, D. E. Shape effects of filaments versus spherical particles in flow and drug delivery. *Nature Nanotechnology* 2, 249-255 (2007).
22. Khan, S., Sur, S., Newcomb, C. J., Appelt, E. A. & Stupp, S. I. Self-assembling glucagon-like peptide 1-mimetic peptide amphiphiles for enhanced activity and proliferation of insulin-secreting cells. *Acta Biomaterialia* 8, 1685-1692 (2012).
23. Whitmore, L. & Wallace, B. A. Protein secondary structure analyses from circular dichroism spectroscopy: Methods and reference databases. *Biopolymers* 89, 392-400 (2008).
24. Koehl, P. & Levitt, M. Structure-based conformational preferences of amino acids. *Proceedings of the National Academy of Sciences of the United States of America* 96, 12524-12529 (1999).
25. Paramonov, S. E., Jun, H.-W. & Hartgerink, J. D. Self-assembly of peptide-amphiphile nanofibers: The roles of hydrogen bonding and amphiphilic packing *Journal of the American Chemical Society* 128, 7291-7298 (2006).
26. Fuguet, E., Ràfols, C., Rosés, M. & Bosch, E. Critical micelle concentration of surfactants in aqueous buffered and unbuffered systems. *Analytica Chimica Acta* 548, 95-100 (2005).
27. MacPhee, C. E. & Woolfson, D. N. Engineered and designed peptide-based fibrous biomaterials. *Current Opinion in Solid State and Materials Science* 8, 141-149 (2004).
28. Forms, P., Lauer-Fields, J. L., Gao, S. & Fields, G. B. Induction of protein-like molecular architecture by monoalkyl hydrocarbon chains. *Biopolymers* 54, 531-546 (2000).
29. Eisenberg, D., Wilcox, W., Eshita, S. M., Pryciak, P. M., Ho, S. P. & DeGrado, W. F. The design, synthesis, and crystallization of an alpha-helical peptide. *Proteins: Structure, Function, and Genetics* 1, 16-22 (1986).
30. Ho, S. P. & Degrado, W. F. Design of a 4-helix bundle protein: Synthesis of peptides which self-associate into a helical protein. *Journal of the American Chemical Society* 109, 6751-6758 (1987).
31. Cella, N., Contreras, A., Latha, K., Rosen, J. M. & Zhang, M. Maspin is physically associated with 1 integrin regulating cell adhesion in mammary epithelial cells. *The FASEB Journal* 20, 1510-1512 (2006).
32. Bass, R., Wagstaff, L., Ravenhill, L. & Ellis, V. Binding of extracellular maspin to 1 integrins inhibits vascular smooth muscle cell migration. *Journal of Biological Chemistry* 284, 27712-27720 (2009).
33. Arnaoutova, I. & Kleinman, H. K. In vitro angiogenesis: endothelial cell tube formation on gelled basement membrane extract. *Nature Protocols* 5, 628-635 (2010).
34. West, D. C., Thompson, W. D., Sells, P. G. & Burbridge, M. F. Angiogenesis assays using chick chorioallantoic membrane. Methods in Molecular Medicine 46, 107-129 (2001).
35. Binetruy-Tournaire, R., Demangel, C., Malavaud, B., Vassy, R., Rouyre, S., Kraemer, M., Plouët, J., Derbin, C., Perret, G., and Mazié, J. C. Identification of a peptide blocking vascular endothelial growth factor (VEGF)-mediated angiogenesis. The EMBO Journal 19, 1525-1533 (2000).
36. Brigati, C., Morini, M., Benelli, R., Minghelli, S., Noonan, D. M., Dell'Eva, R., and Albini, A. Anti-angiogenic peptide. U.S. Patent Application 20110144022A1, June 2011.
37. Malone, T. E., Gray, G. S., Petro, J., Hunt, A. J., Donner, A. L., Bauer, S. I., Carson, H. F., and Sharpe, R J Inhibition of angiognnesis by recombinant human platelet factor-4 and related peptides. Science 247, 77-79 (1990).
38. Mayo, K. H., van der Schaft, D. W., and Griffioen, A. W. Designed beta-sheet peptides that inhibit proliferation and induce apoptosis in endothelial cells. Angiogenesis 4, 45-51 (2001).
39. Sakamotu, N., Iwahana, M., Tanaka, N. G., and Osada, Y. Inhibition of angiogenesis and tumor growth by a synthetic laminin peptide, CDPGYIGSR-NH2. Cancer Research 51, 903-906 (1991).
40. Tolsma, S. S., Volpert, O. V., Good, D. J., Frazier, W. A., Polverini, P. J., and Bouck, N. Peptides derived from two separate domains of the matrix protein thrombospondin-1 have anti-angiogenic activity. Journal of Cell Biology 122, 497-511 (1993).
41. Woltering, E. A., Barrie, R., O'Dorisio, T. M., Arce, D., Ure, T., Cramer, A., Holmes, D., Robertson, J., and Fassler, L. Somatostain analogues inhibit angiogenesis in the chick chorioallantoic membrane. Journal of Surgical Research 50, 245-251 (1991)

We Claim:

1. A composition, the composition comprising: (a) a hydrophobic tail; (b) a peptide sequence capable of beta-sheet formation; (c) a flexible peptide linker; and (d) a peptide configured to inhibit angiogenesis.

2. The composition as in claim 1, wherein the flexible linker comprises GG.

3. The composition as in claim 1, wherein the hydrophobic tail is a C6-C22 alkyl group.

4. The composition as in claim 1, wherein the peptide sequence capable of beta-sheet formation comprises VVAA (SEQ ID NO: 19).

5. The composition as in claim 1, wherein the peptide configured to inhibit angiogenesis comprises a PPPXHPPH-PPP (SEQ ID NO: 20) sequence of amino acids, wherein P is a polar amino acid, H is an apolar amino acid and X is a glycine.

6. The composition as in claim 1, wherein the peptide configured to inhibit angiogenesis comprises a maspin g-helix.

7. The composition as in claim 1, wherein the peptide comprises ESTGLEKIEKQ (SEQ ID NO: 1).

8. The composition as in claim 1, wherein the peptide comprises EDESTGLEKIEKQLN (SEQ ID NO: 2).

9. A nanostructure, comprising the composition of claim 1 and further comprising a second peptide amphiphile.

10. A method of inhibiting angiogenesis, comprising contacting endothelial cells with the composition as in claim 1 in an amount effective to inhibit angiogenesis.

11. A composition, the composition comprising: (a) a hydrophobic tail; (b) a peptide sequence comprising VA and capable of beta-sheet formation; and (c) a peptide configured to inhibit angiogenesis.

12. The composition as in claim 11, wherein the peptide sequence capable of beta-sheet formation comprises VVAA (SEQ ID NO: 19).

13. The composition as in claim 11, further comprising a flexible linker between the peptide sequence comprising VA and capable of beta-sheet formation and the peptide configured to inhibit angiogenesis.

14. The composition as in claim 13, wherein the flexible linker comprises GG.

15. The composition as in claim 11, wherein the hydrophobic tail is a C6-C22 alkyl group.

16. The composition as in claim 11, wherein the peptide configured to inhibit angiogenesis comprises a PPPXHPPH-PPP (SEQ ID NO: 20) sequence of amino acids, wherein P is a polar amino acid, H is an apolar amino acid and X is a glycine.

17. The composition as in claim 11, wherein the peptide configured to inhibit angiogenesis comprises a maspin g-helix.

18. The composition as in claim 11, wherein the peptide comprises ESTGLEKIEKQ (SEQ ID NO: 1).

19. The composition as in claim 11, wherein the peptide comprises EDESTGLEKIEKQLN (SEQ ID NO: 2).

20. A nanostructure, comprising the composition of claim 11 and further comprising a second peptide amphiphile.

21. A method of inhibiting angiogenesis, comprising contacting endothelial cells with the composition as in claim 11 in an amount effective to inhibit angiogenesis.

* * * * *